US00PP33480P2

(12) United States Plant Patent
Kolster et al.

(10) Patent No.: US PP33,480 P2
(45) Date of Patent: Sep. 14, 2021

(54) ***HYDRANGEA* PLANT NAMED 'JONG 02'**

(50) Latin Name: *Hydrangea macrophylla*
Varietal Denomination: Jong 02

(71) Applicants: Peter Kolster, Boskoop (NL); Kees Eveleens, Aalsmeer (NL)

(72) Inventors: Peter Kolster, Boskoop (NL); Kees Eveleens, Aalsmeer (NL)

(73) Assignee: De Jong Plant B.V., Boskoop (NL)

( * ) Notice: Subject to any disclaimer, the term of this patent is extended or adjusted under 35 U.S.C. 154(b) by 0 days.

(21) Appl. No.: 17/115,549

(22) Filed: Dec. 8, 2020

(30) Foreign Application Priority Data

Aug. 4, 2020 (QZ) ..... PBR 2020/1683

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* plant named 'Jong 02' that is characterized by its foliage that are black-green to green-black in color, its strong branches and compact plant habit, its lacecap shaped inflorescences that become flattened globular when they mature, and its sterile flowers with sepals that are deep red in color.

2 Drawing Sheets

Botanical classification: *Hydrangea macrophylla.*
Varietal denomination: 'Jong 02'.

CROSS-REFERENCE TO A RELATED APPLICATION

This application claims priority to European Community Plant Variety Office (CPVO) Plant Breeder's Rights Application No. 2020/1683 filed on Aug. 4, 2020, under 35 U.S.C. 119(f), the entire contents of which is incorporated by reference herein.

BACKGROUND OF THE INVENTION

The present invention relates to a new and distinct cultivar of *Hydrangea macrophylla* and will be referred to hereafter by its cultivar name, 'Jong 02'. 'Jong 02' represents a new bigleaf *Hydrangea*, a perennial shrub grown for landscape use and as a potted plant.

'Jong 02' was derived from an ongoing controlled breeding program directed by the Inventors. An objectives of the breeding program included developing new cultivars of *Hydrangea* with desirable inflorescence and foliage coloration and plant shape.

'Jong 02' arose from a controlled cross made by the Inventors in Rijsenhout, The Netherlands in May of 2015 between *Hydrangea macrophylla* cultivars 'Dark Angel' (not patented) as the female parent and an unnamed and unpatented proprietary plant in the Inventors' breeding program as the male parent. 'Jong 02' was selected as a single unique plant from amongst the resulting seedlings in June of 2017.

Asexual propagation of the new cultivar was first accomplished by softwood stem cuttings by the Inventors in August of 2017 in Boskoop, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Jong 02' as a unique cultivar of *Hydrangea macrophylla.*

1. 'Jong 02' exhibits foliage that are black-green to green-black in color.
2. 'Jong 02' exhibits strong branches and a compact plant habit.
3. 'Jong 02' exhibits lacecap shaped inflorescences that become flattened globular when they mature.
4. 'Jong 02' exhibits sterile flowers with sepals that are deep red in color.

The female parent of 'Jong 02' differs from 'Jong 02' in having foliage that is lighter black-green in color, inflorescences do not become flattened when they mature, and sterile flowers with sepals that are purple-red in color. The male parent of 'Jong 02' differs from 'Jong 02' in having foliage that is dark green in color, mophead shaped inflorescences and sterile flowers that are purple-red in color. 'Jong 02' can be most closely compared to the *Hydrangea macrophylla* cultivars 'Merveille Sanguine' (not patented) and 'Red Angel' (not patented). 'Merveille Sanguine' is similar to 'Jong 02' in having foliage that is dark in color. 'Merveille Sanguine' differs from 'Jong 02' in having foliage that is dark green-purple (no black tones) in color turning deep red in fall, mophead shaped inflorescences and, sterile flowers with sepals that are purple-red in color. 'Red Angel' is similar to 'Jong 02' in having sterile flowers with sepals that are deep red in color. 'Red Angel' differs from 'Jong 02' in having foliage that is dark green-purple (no black tones) in color and mophead shaped inflorescences.

BRIEF DESCRIPTION OF THE DRAWINGS

The accompanying colored photographs illustrate the overall appearance and distinct characteristics of the new *Hydrangea*. The photographs were taken of three-year-old plants of 'Jong 02' as grown in a greenhouse in a 27-cm container in Boskoop, The Netherlands.

The photograph in FIG. 1 provides a side view of 'Jong 02' in bloom.

Figure 1:
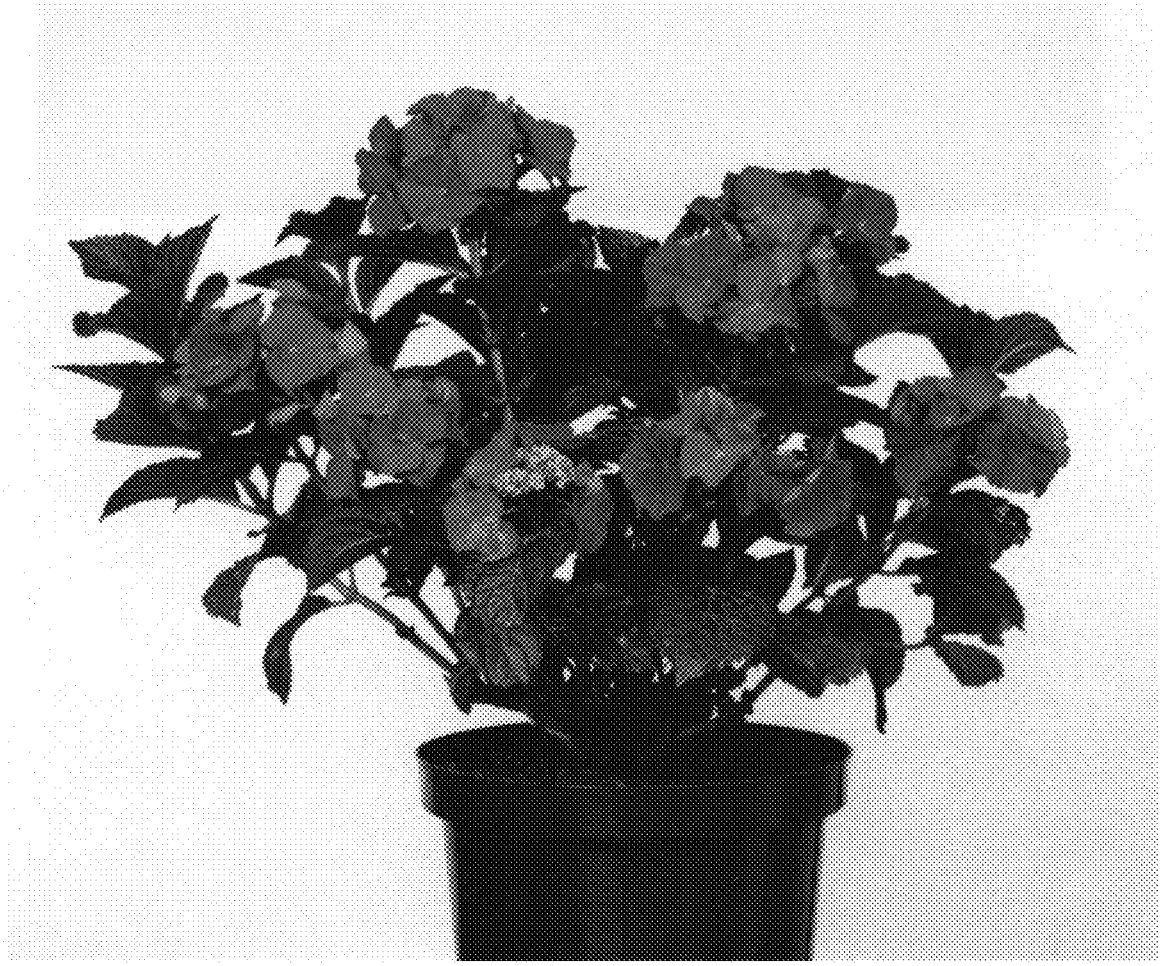
Figure 2:
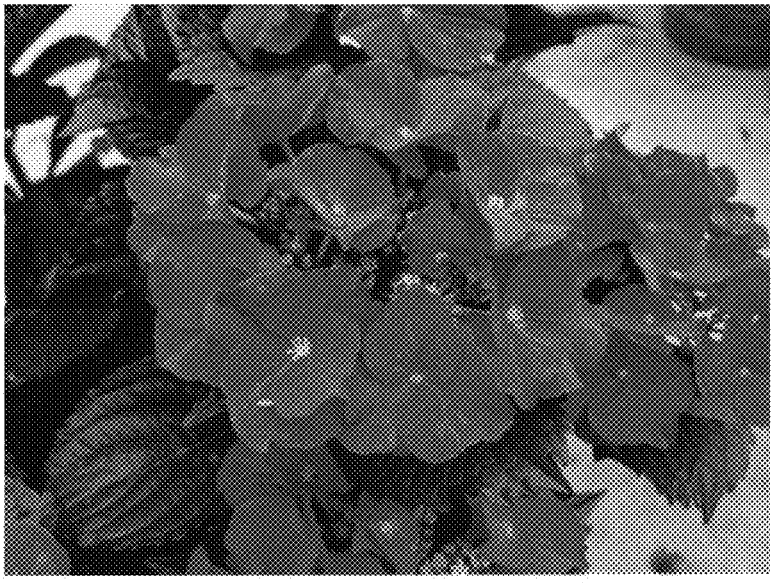

The photograph in FIG. 2 provides a close-up view of the inflorescences of 'Jong 02'.

Figure 3:
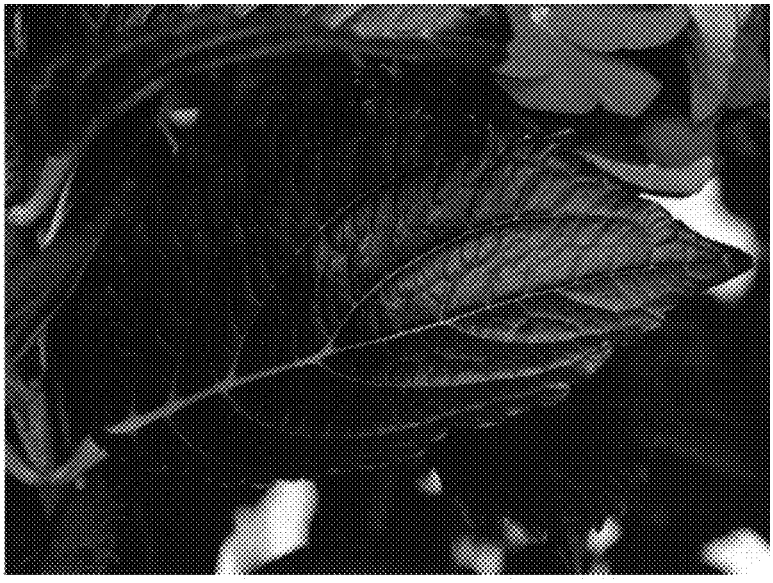

The photograph in FIG. 3 provides a close-up view of the foliage of 'Jong 02'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of three-year-old plants of 'Jong 02' as grown in a greenhouse in 27-cm containers in Boskoop, The Netherlands. Plants are not grown under bluing conditions. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—June into September in The Netherlands.

*Plant type.*—Deciduous shrub.

*Plant habit.*—Broad spreading, upright, compact, flattened globular in shape.

*Height and spread.*—An average of 46.7 cm in height and 67.6 cm in spread.

*Hardiness.*—At least U.S.D.A. Zones 5 to 9.

*Diseases and pests.*—No susceptibility and resistance to diseases or pests has been observed.

*Root description.*—Fine and fibrous, 161C in color.

*Propagation.*—Stem cuttings.

*Root development.*—An average of 4 weeks for root initiation with a young rooted plant produced in an average of 18 weeks.

*Growth rate and vigor.*—Moderate to high.

Stem description:

*Stem shape.*—Rounded.

*Stem strength.*—Strong.

*Stem color.*—Young; 146B, mature 146B, internodes slightly tinged N186A, older bark 199C and 200B.

*Stem size.*—An average of 28.1 cm in length (excluding inflorescence) and 6 mm in diameter.

*Stem surface.*—Glabrous, moderately lenticellate, lenticels; an average of 1 mm in length and 0.75 mm in diameter, N186C in color, fasciation absent.

*Stem aspect.*—Upright, held in an average angle of 65° to the soil, varying between 40° and 90°.

*Internode length.*—An average of 4.7 cm.

*Branching.*—Freely branching with an average of 21 lateral branches.

Foliage description:

*Leaf shape.*—Ovate to broadly ovate to broadly elliptical in shape.

*Leaf arrangement.*—Opposite.

*Leaf division.*—Simple.

*Leaf base.*—Attenuate.

*Leaf apex.*—Apiculate.

*Leaf margins.*—Coarsely serrate.

*Leaf venation.*—Pinnate, color; young upper surface 145A, young lower surface 152A, mature upper surface 146B to 146C, mature lower surface 146C, slightly tinged N199B.

*Leaf size.*—An average of 11.6 cm in length and 8.1 cm in width.

*Leaf attachment.*—Petiolate.

*Leaf number.*—An average of 16 per lateral stem.

*Leaf surface.*—Both surfaces; glabrous and moderately rugose.

*Leaf color.*—Young foliage; upper surface between 200A and 203B with a hue of N186A, lower surface between N186C and 200A, mature foliage; upper surface between 200A and 203B with older leaves 147A with a hue of 203B, tinged 187A at the top, lower surface 200C to 200D with older leaves 148A to 148B.

*Petioles.*—An average of 1.2 cm in length and 5 mm in diameter, upper and lower surface 146D in color, surface smooth and slightly glossy.

Inflorescence description:

*Inflorescence type.*—Terminal flattened globular compound corymb of single sterile and fertile flowers, lacecap in form.

*Lastingness of inflorescence.*—Sterile flowers; persistent for an average of 6 weeks, fertile flowers; self-cleaning for an average of 5 days.

*Inflorescence number.*—One per lateral stem.

*Inflorescence size.*—An average of 7.2 cm in height and 13.7 cm in diameter.

*Flower number.*—An average of 14 sterile flowers, an average of 125 fertile flowers.

*Flower fragrance.*—Fertile flowers have a slightly sweet and moldy fragrance.

*Flower aspect.*—Upright to outward.

*Flower size.*—Sterile flowers; an average of 5.5 cm in diameter and 2 cm in depth, fertile flowers; 8 mm in diameter and depth.

*Flower type.*—Rotate, fertile flowers dropped when maturing.

*Flower buds.*—Sterile flowers; an average of 8 mm in length and 1.4 cm in diameter, cup shaped, color; 60A to 60B, base 145B to 145C, fertile flowers; an average of 5 mm in length, 4 mm in diameter, obovate in shape, color; 60D, striped 60A, base 151A, tipped 177A.

*Peduncles.*—Moderately strong, round in shape, an average of 4.5 cm in length and 3 mm in width, main peduncle held straight on top of the lateral branch, lateral peduncle held in an average angle of 25° from vertical to main peduncle, 146B and tinged N186A in color, surface dull and densely pubescent; covered with thin pubescence an average of 0.2 mm in length and too small to measure color.

*Pedicels.*—Sterile flowers; held primarily at an average angle of 50° to upright from peduncle, an average of 2.6 cm in length and 2 mm in diameter, moderately strong, color; 177B, tinged 182A, surface dull and densely pubescent; covered with thin pubescence an average of 0.2 mm in length and too small to measure color, fertile flowers; held primarily at an average angle of 30° to upright from peduncle, an average of 3.5 cm in length and 1 mm in diameter, moderately strong, color; 151A to 151B, dull and densely pubescent surface covered with thin pubescence an average of 0.2 mm in length and too small to measure color.

*Petals.*—Sterile flowers; an average of 4, rotate in arrangement, acute apex, cuneate base, entire margins, ovate in shape, strongly concave in aspect, average of 3 mm in length and 2 mm in width, both surfaces; glabrous, matte, color; when opening upper surface 70B, margins 75D, when opening lower surface 63B to 63D, when fully open upper surface 70B, base and margins 75D, when fully open lower surface 63B to 63D, fertile flowers; an average of 5, rotate in arrangement, acute apex, cuneate base, entire margins, ovate in shape, strongly concave in aspect, average of 4 mm in length and 2 mm in width, both surfaces; glabrous, matte, color; when opening and fully upper surface 70B and 70D, base and margins 75D, when opening and fully open lower surface 59D, fading towards the top N186C.

*Sepals.*—Sterile flowers; 4, occasionally 5, cruciform, rotate arrangement, bluntly acute to short apiculate apex, broadly cuneate to truncate base, margins are entire and coarsely undulate, broadly ovate to reniform in shape, an average of 3.1 cm in length and 3.9 cm in width, both surfaces glabrous and dull, color; when opening upper surface 60A to 60B, when opening lower surface 59D, when fully open upper surface 53A, central portion slightly tinged 187C, fading to 59A, moderately to strongly tinged 187B, when fully open lower surface 184C and 184D, fading to 184A, fertile flowers; 5, occasionally 6, rotate arrangement, broadly acute apex, cuneate base, margins are entire, deltoid in shape, an average of 3 mm in length and 1.5 cm in width, both surfaces glabrous and dull, color; when opening upper surface 151A to 151B, when opening lower surface 151A, tipped 177A, when fully open upper surface 151B, when fully open lower surface 151B, tipped 174A.

Reproductive organs:

*Gynoecium.*—Sterile flowers; pistil; 2, occasionally 3, average of 1 mm in length, stigma; club-shaped, 155A in color, style; 0.5 mm in length, 59B in color, ovary; 63D in color, fertile flowers; pistil; 2, occasionally 3, average of 1 mm in length, stigma; club-shaped, 155A in color, style; 0.5 mm in length, 59B in color, ovary; 151B in color.

*Androecium.*—Sterile flowers; an average of 8 stamens, filaments; an average of 3 mm in length and NN155D in color, anthers; broadly oblong in shape, an average of 0.75 mm in length and 155A in color, pollen; moderate in quantity and 157A in color, fertile flowers; an average of 10 stamens, filaments; an average of 4 mm in length and NN155D in color, anthers; broadly oblong in shape, an average of 0.75 mm in length and 155A in color, pollen; moderate in quantity and 157A in color.

*Fruit and seed.*—None observed to date.

It is claimed:

1. A new and distinct cultivar of *Hydrangea* plant named 'Jong 02' substantially as herein illustrated and described.

* * * * *